United States Patent
Ceylan et al.

(10) Patent No.: US 11,519,014 B2
(45) Date of Patent: Dec. 6, 2022

(54) SPECIFIC SUBSTRATE OF AN ALDH ISOENZYME

(71) Applicants: ADVANCED BIODESIGN, Saint-Priest (FR); Centre national de la recherche scientifique, Paris (FR); Université Claude Bernard Lyon 1, Villeurbanne (FR); Jean-Yves Quash, Gometz la Ville (FR)

(72) Inventors: Ismail Ceylan, Saint-Priest (FR); Guillaume Martin, Saint-Priest (FR); Gérard Quash, Craponne (FR); Milleidys Perez-Alea, Saint-Priest (FR); Guy Fournet, Lyons (FR)

(73) Assignee: ADVANCED BIODESIGN, Saint Priest (FR)

( * ) Notice: Subject to any disclaimer, the term of this patent is extended or adjusted under 35 U.S.C. 154(b) by 497 days.

(21) Appl. No.: 16/320,071

(22) PCT Filed: Jul. 27, 2017

(86) PCT No.: PCT/EP2017/068985
§ 371 (c)(1),
(2) Date: Jan. 23, 2019

(87) PCT Pub. No.: WO2018/019927
PCT Pub. Date: Feb. 1, 2018

(65) Prior Publication Data
US 2019/0233871 A1 Aug. 1, 2019

(30) Foreign Application Priority Data
Jul. 28, 2016 (FR) ...................... 1657324

(51) Int. Cl.
C12Q 1/00 (2006.01)
C12Q 1/32 (2006.01)

(52) U.S. Cl.
CPC .............. *C12Q 1/007* (2013.01); *C12Q 1/32* (2013.01); *C12Q 2334/20* (2013.01); *C12Q 2334/40* (2013.01)

(58) Field of Classification Search
None
See application file for complete search history.

(56) References Cited

U.S. PATENT DOCUMENTS 3,378,463 A * 4/1968 Guilbault ................. C12Q 1/34
435/20
2012/0237931 A1 9/2012 Katz
(Continued)

FOREIGN PATENT DOCUMENTS

EP 0 989 137 A2 3/2000
JP 2010-523476 A 7/2010
(Continued)

OTHER PUBLICATIONS

Rotman et al., Proc. Nat'l. Acad. Sci. USA 55(1): 134-141 (1966).*
(Continued)

*Primary Examiner* — Erin M. Bowers
(74) *Attorney, Agent, or Firm* — Troutman Pepper Hamilton Sanders LLP

(57) ABSTRACT

The invention relates to a specific substrate on an ALDH isoenzyme, to a composition comprising at least one such substrate, to a diagnostic marker comprising such a substrate, and to the uses thereof and associated methods.

7 Claims, 5 Drawing Sheets

(56) References Cited

U.S. PATENT DOCUMENTS

2014/0072990 A1 3/2014 Urano et al.
2015/0369738 A1 12/2015 Pomper et al.

FOREIGN PATENT DOCUMENTS

| | | |
|---|---|---|
| JP | 2011-184303 A | 9/2011 |
| JP | 2012-506439 A | 3/2012 |
| JP | 2012-506856 A | 3/2012 |
| WO | 95/00660 A1 | 1/1995 |
| WO | 00/34507 A1 | 6/2000 |
| WO | 2008/112164 A2 | 9/2008 |
| WO | 2009/031708 A1 | 3/2009 |
| WO | 2010/028175 A1 | 3/2010 |
| WO | 2010/048144 A2 | 4/2010 |
| WO | 2010/062308 A1 | 6/2010 |
| WO | 2014/130834 A1 | 8/2014 |

OTHER PUBLICATIONS

Kitson et al., Enzymology and Molecular Biology of Carbonyl Metabolism 6, chapter 23, pp. 201-208 (1996).*

Kitson et al., Biochem. J. 316: 225-232 (1996).*

French Search Report for Application No. FR 1657324 dated Mar. 21, 2017.

International Search Report for Application No. PCT/EP2017/068985 dated Oct. 30, 2017.

Wierzchowski et al., "Fluorimetric Detection of Aldehyde Dehydrogenase Activity in Human Blood, Saliva, and Organ Biopsies and Kinetic Differentiation between Class I and Class III Isozymes", Analytical Biochemistry, vol. 245, No. 1, Feb. 1, 1997, pp. 69-78.

Eshghi et al., "Synthesis of fluorescein aromatic esters in the presence of P205/Si02 as catalyst and their hydrolysis studies in the presence of lipase", Dyes and Pigments, vol. 89, No. 2, May 1, 2011, pp. 120-126.

Jones at el., "Assessment of aldehyde dehydrogenase in viable cells", Blood, vol. 85, No. 10, May 15, 1995, pp. 2742-2746.

Ge, F., et al. "Synthesis and study on hydrolytic properties of fluorescein esters" Dyes and Pigments 72:322-236 (2007).

Minn, I., et al. "A red-shifted fluorescent substrate for aldehyde dehydrogenase" Nature Communications pp. 1-9 (2014).

Alnouti, Y. et al., "Tissue Distribution, Ontogeny, and Regulation of Aldehyde Dehydrogenase (Aldh) Enzymes mRna by Prototypical Microsomal Enzyme Inducers in Mice" Toxicological Sciences 101(1):51-64 (2008).

He, Feng-Ying, et al. "Studies on Crystal Structure and Hydrolysis Features of the Fluorescein Dibenzoate" Acta Chemica Sinica 51:119-124(1993), with English abstract.

Wang, Liufang, et al. "Synthesis of Some Fluorescein Diesters and Their Bilogical Fluorescence Activity" Chinese Journal of Luminescence 8(4):317-322 (1987), with English abstract.

Imaging Science and Photochemistry, vol. 32, No. 1 (Jan. 2014) China Academic Journal Electronic Publishing House in Chinese.

* cited by examiner

SPECIFIC SUBSTRATE OF AN ALDH ISOENZYME

CROSS REFERENCE TO RELATED APPLICATIONS

This application is the National Stage of International Application PCT/EP2017/068985 filed Jul. 27, 2017, which published as WO 2018/019927 on Feb. 1, 2018. The International Application claims priority to French Application No. 16 57324 filed Jul. 28, 2016, all of these applications are incorporated herein in their entirety.

FIELD OF THE INVENTION

The present invention relates to a specific substrate of an ALDH isoenzyme, to a composition comprising at least one such substrate, to a diagnostic marker comprising such a substrate, and to their associated uses and methods.

BACKGROUND

Aldehyde dehydrogenases (ALDHs) are a group of enzymes that catalyze the oxidation (dehydrogenation) of aldehydes. To date, nineteen genes encoding ALDHs have been identified in the human genome. These genes participate in a wide variety of biological processes, including the detoxification of aldehydes generated exogenously and endogenously. ALDHs are found in all subcellular regions including the cytosol, mitochondria, endoplasmic reticulum, and nucleus, many of which are found in more than one compartment. Most ALDHs have a broad tissue distribution and exhibit distinct substrate specificity.

Generally considered as detoxifying enzymes, ALDHs have been shown to protect against aldehyde-induced cytotoxicity. ALDHs also play a central role in physiological functions and processes, such as embryogenesis and development.

In particular, the ALDH1 isoenzyme plays a central role in embryogenesis and development by mediating retinoic acid signaling. It is also involved in the detoxification of methional while ALDH3 is involved in that of 4-hydroxynonal, wherein both compounds are endogenous apoptogenic aldehydes. ALDH1 and ALDH3 are also related to the cellular defense mechanisms against UV radiation inducing damage in the ocular tissue. The ALDH2 isoenzyme is a mitochondrial isoenzyme mainly related to the detoxification of acetaldehyde in the second stage of alcohol metabolism.

More than 20 years ago, ALDHs were studied for their potential use as a universal marker of normal and cancerous stem cells, since some of the ALDH isoenzymes have been identified as key elements of these cells. For example, ALDH1 has been shown to be high in hematopoietic stem cells and could be used to isolate them.

A common method used to identify and isolate stem cells through their high ALDH activity is the use of the ALDE-FLUOR™ test (Stemcell Technologies Inc.). This ALDE-FLUOR™ test uses a fluorescent substrate that can be metabolized by many isoenzymes of ALDH.

In this test, the substrate of ALDH: BODIPY-aminacetaldehyde (BAAA) is converted to BODIPY-aminoacetate in the presence of ALDH, which accumulates in the cells and increases their fluorescence by the emission of a green color.

However, ALDEFLUOR™ does not differentiate between the different isoenzymes of ALDH.

Despite active research, the role of the different isoenzymes of ALDH in different areas such as stem cells or oncology, remains enigmatic. Understanding the metabolism of different isoenzymes in the control of cell phenotype and during development, tissue homeostasis or repair, as well as in carcinogenesis, may yet open important perspectives in tissue biology.

There is therefore a need to identify new substrates that would be specific to the different isoenzymes of ALDH.

SUMMARY

It is in this context that the inventors of the present invention have discovered a tool for identifying the different isoenzymes of ALDH, by developing new specific substrates thereof.

The object of the present invention is therefore a specific substrate for an ALDH isoenzyme comprising a compound:
(a) of formula (I): R—COO-A (I) resulting from the esterification of a fluorescent tracer A-OH with an acylating agent derived from the corresponding acid RCOOH, in which R is chosen to form retinoate, propionate, octanoate, benzoate, 4-aminobutyrate, hexanoate, 4-diethylaminobenzoate or 4-hydroxy-2-nonenoate; or
(b) of formula (II):

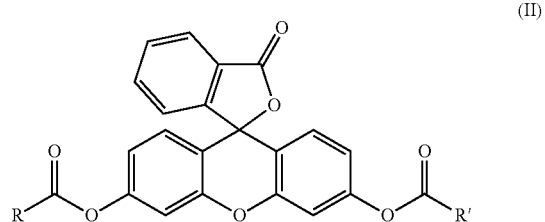

in which R and R', which are identical or different, are chosen in order to form retinoate, propionate, octanoate, benzoate, 4-aminobutyrate, hexanoate, 4-diethylaminobenzoate or 4-hydroxy-2-nonenoate.

A specific substrate is thus described for an ALDH isoenzyme comprising a compound:
(a) of formula (I): R—COO-A (I); or
(b) of formula (II):

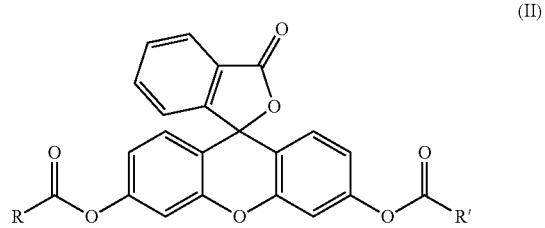

in which:
R and R', which are identical or different, are chosen in order to form retinoate, propionate, octanoate, benzoate, 4-aminobutyrate, hexanoate, 4-diethylaminobenzoate or 4-hydroxy-2-nonenoate; and
A-OH is a fluorescent tracer.
A is thus the esterified form of A-OH which is a fluorescent tracer, when the latter is free.

The present invention also relates to the use of a specific substrate according to the invention for quantifying an ALDH isoenzyme in a cell population.

The present invention also relates to the use of a specific substrate according to the invention for distinguishing healthy stem cells from cancer stem cells.

The present invention also relates to the use of a specific substrate according to the invention for characterizing the different stages of a cancer or the different stages of stem cell differentiation.

The present invention also relates to a composition comprising at least one specific substrate according to the invention.

The present invention also relates to a diagnostic marker comprising a specific substrate according to the invention.

The present invention also relates to the use of a marker according to the invention for the diagnosis of a disease involving deregulation of an ALDH isoenzyme. In particular, the marker is used to determine whether a subject is capable of responding to therapy that inhibits the activity of an ALDH isoenzyme and/or is directed against cancer stem cells.

The present invention also relates to a method for distinguishing cells expressing at least one ALDH isoenzyme in a cell population, wherein the method comprises:
 (a) bringing the cell population into contact with at least one specific substrate according to the invention,
 (b) measuring the fluorescence of the cell population; and
 (c) identifying cells with increased fluorescence relative to the fluorescence of the cell population before this population is brought into contact with at least one specific substrate according to the invention.

The present invention also relates to a kit for quantifying an ALDH isoenzyme comprising at least one specific substrate according to the invention.

As indicated above, the invention relates to a specific substrate for an ALDH isoenzyme comprising a compound:
 (a) of formula (I): R—COO-A (I) resulting from the esterification of a fluorescent tracer A-OH with an acylating agent derived from the corresponding acid RCOOH, in which R is chosen in order to form retinoate, propionate, octanoate, benzoate, 4-aminobutyrate, hexanoate, 4-diethylaminobenzoate or 4-hydroxy-2-nonenoate; or
 (b) of formula (II):

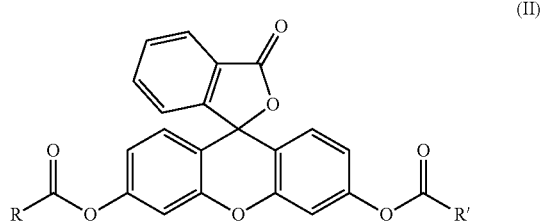

(II)

in which R and R', which are identical or different, are chosen in order to form retinoate, propionate, octanoate, benzoate, 4-aminobutyrate, hexanoate, 4-diethylaminobenzoate or 4-hydroxy-2-nonenoate.

The compound of formula (II) may also be described as having the formula: R—COO-A-OOC—R', in which the fluorescent tracer is of formula HO-A-OH and is fluorescein.

By "specific substrate of an ALDH isoenzyme" is meant a chemical molecule that will interact specifically with a particular ALDH isoenzyme such as ALDH1 or ALDH3, for example, in order to produce a chemical reaction which, in the context of the present invention, will make it possible to release a fluorescent molecule (A-OH) thus making it possible to identify with certainty the particular ALDH isoenzyme. Thus, in the context of the invention, the specific substrate will be cleaved by an ALDH isoenzyme which will allow the release of the fluorescent tracer A-OH.

The specific substrate according to the invention results from the esterification of the fluorescent tracer A-OH with an acylating agent derived from the corresponding acid RCOOH or R'COOH.

For example, in the case where R and/or R', whose acid RCOOH and/or R'COOH is a propionic acid, the corresponding ester is propionate, in the case where R and/or R', whose RCOOH acid and/or R'COOH is a hexanoic acid, the ester corresponding a hexanoate, in the case where R and/or R' whose acid RCOOH and/or R'COOH is a retinoic acid, the corresponding ester is retinoate, in the case where R and/or R' whose acid RCOOH and/or R'COOH is a benzoic acid, the corresponding ester is benzoate, in the case where R and R' whose acid RCOOH and/or R'COOH is a 4-diethylaminobenzoic acid, the corresponding ester is 4-diethylaminobenzoate, in the case where R and R' whose acid RCOOH and/or R'COOH is a 4-hydroxy-2-nonenoic acid, the corresponding ester is 4-hydroxy-2-nonenoate, in the case where R and/or R' whose acid RCOOH and/or R'COOH is 4-aminobutanoic acid, the corresponding ester is 4-aminobutyrate.

In parallel, for example, in the case where R and/or R' is a heptyl, the corresponding ester is octanoate, in the case where R and/or R' is an ethyl, the corresponding ester is propionate, in the case where R and or R' is phenyl, the corresponding ester is benzoate, in the case where R and/or R' is 3-aminopropyl, the corresponding ester is 4-aminobutyrate, etc.

"A" is defined such that the hydroxylated form of A (which is A-OH), is a fluorescent tracer. The latter forms an ester with the specific substrates forming formulas (I) R—COO-A and (II) R—COO-A-OOC—R' which, after cleavage of the ester function, leads to the release of RCOOH acid. and/or R'COOH and the fluorescent tracer A-OH.

Table 1 below gives the structure of the substituents R and R' according to the invention, linked to the fluorescent tracer. The table also indicates the specificity of each substrate with respect to the ALDH isoenzymes.

TABLE 1

| Acylating agent (R/R') | Specific ALDH |
|---|---|
| | ALDH1 |
| | ALDH1 |
| | ALDH1 |

TABLE 1-continued

| Acylating agent (R/R') | Specific ALDH |
|---|---|
| benzoate structure | ALDH3 |
| 4-diethylaminobenzoate structure | ALDH3 |
| 4-hydroxy-2-nonenoate structure | ALDH3 |
| 4-aminobutyrate structure | ALDH9 |

By "fluorescent tracer" is meant a chemical compound that may be identified by fluorescence. In particular, a fluorescent tracer according to the invention is a fluorochrome or a fluorophore, i.e. a chemical substance capable of emitting fluorescence light after excitation.

In the context of the present invention, the fluorophore will be released under the action of an ALDH isoenzyme.

Fluorophores are well known to those skilled in the art (see, for example, Manafi (2000) Int. J. Food Microbiol. 60: 205-218).

Various fluorescent tracers according to the invention are shown in Table 2 below.

TABLE 2

| Tracer | Structures and formulas | Emission color |
|---|---|---|
| 7-hydroxycoumarine | Formula = $C_9H_6O_3$ | blue |
| Fluorescein | Formula = $C_{20}H_{12}O_5$ | green |
| 2-methyl-4-methoxy-Tokyo Green | Formula = $C_{21}H_{16}O_4$ | green |
| Resorufin | Formula = $C_{12}H_7NO_3$ | red |

In particular, in the context of the present invention, A-OH is chosen from 7-hydroxycoumarin, a fluorophore of the tokyo green family, in particular 2-methyl-4-methoxy-Tokyo Green, resorufin and fluorescein. These tracers are all known to those skilled in the art and are either commercially available or can be synthesized by methods well known to those skilled in the art.

In particular, 2-methyl-4-methoxy-Tokyo Green is also named 6-Hydroxy-9-(4-methoxy-2-methylphenyl)-3H-xanthen-3-one, 2-Me-4-OMe Tokyo Green or 2-Me-4-OMe TG.

Thus, mention may be made of the following molecules as a specific substrate according to the present invention: resorufin retinoate, resorufine propionate, resorufine octanoate, resorufin benzoate, resorufine 4-aminobutyrate, resorufin hexanoate, resorufin 4-diethylaminobenzoate or resorufin 4-hydroxy-2-nonenoate, 7-hydroxycoumarin retinoate, 7-hydroxycoumarin propionate, 7-hydroxycoumarin octanoate, 7-hydroxycoumarin benzoate, 4-hydroxycoumarin 4-aminobutyrate, 7-hydroxycoumarin hexanoate, 7-hydroxycoumarine 4-diethylaminobenzoate or 7-hydroxycoumarine 4-hydroxy-2-nonenoate, 2-methyl-4-methoxy-Tokyo Green retinoate, 2-methyl-4-methoxy-Tokyo Green propionate, 2-methyl-4-methoxy-Tokyo Green octanoate, 2-methyl-4-methoxy-Tokyo Green benzoate, 4-aminobutyrate 2-methyl-4-methoxy-Tokyo Green, 2-methyl-4-methoxy hexanoate Tokyo Green, 2-methyl-4-methoxy-Tokyo Green 4-diethylaminobenzoate or 2-methyl-4-methoxy-Tokyo Green or 4-hydroxy-2-nonenoate, fluorescein di-retinoate, fluorescein di-propionate, fluorescein di-octanoate, fluorescein di-benzoate, fluorescein di-4-aminobutyrate, fluorescein di-hexanoate, fluorescein di-4-diethylaminobenzoate or fluorescein di-4-hydroxy-2-nonenoate.

As previously stated "ALDH" is used for "aldehyde dehydrogenases" and represents a group of dehydrogenase-like enzymes that exist in constitutive and inducible forms.

In human beings, 19 ALDHs have been identified, including as many genes. They are divided into subgroups: ALDH1 comprising ALDH1A1, ALDH1A2, ALDH1A3, ALDH1B1, ALDH1L1 and ALDH1L2, ALDH2, ALDH3 comprising ALDH3A1, ALDH3A2, ALDH3B1 and ALDH3B2, ALDH4, ALDH5, ALDH6, ALDH7, ALDH8, ALDH9, ALDH16, and ALDH18.

In particular, a specific substrate according to the invention is a specific substrate for ALDH1 or ALDH3.

According to one embodiment of the present invention, when the ALDH isoenzyme is ALDH1, R, and R', which are identical or different, are chosen in order to form retinoate, hexanoate or propionate.

In particular, when the ALDH isoenzyme is ALDH1, a specific substrate according to the invention is chosen from among resorufine retinoate, resorufine hexanoate, resorufine propionate, 7-hydroxycoumarin retinoate, 7-hydroxycoumarin hexanoate, 7-hydroxycoumarin propionate, 2-methyl-4-methoxy-Tokyo Green retinoate, 2-methyl-4-methoxy-Tokyo Green hexanoate, 2-methyl-4-methoxy-Tokyo Green propionate, fluorescein di-retinoate, fluorescein dipropionate, fluorescein di-hexanoate.

According to another embodiment of the present invention, when the ALDH isoenzyme is ALDH3, R and R', which are identical or different, are chosen in order to obtain octanoate, 4-hydroxy-2-nonenoate, 4-diethylaminobenzoate or benzoate.

In particular, when the ALDH isoenzyme is ALDH3, a specific substrate according to the invention is chosen from among resorufin octanoate, resorufin 4-hydroxy-2-nonenoate, resorufine benzoate, resorufine 4-diethylaminobenzoate, 7-hydroxycoumarin octanoate, 7-hydroxycoumarine 4-hydroxy-2-nonenoate, 7-hydroxycoumarin benzoate, 7-hydroxycoumarine 4-diethylaminobenzoate, 2-methyl-4-methoxy-Tokyo Green octanoate, 2-methyl-4-methoxy-Tokyo Green 4-hydroxy-2-nonenoate, 2-methyl-4-methoxy-Tokyo Green benzoate, 2-methyl-4-methoxy-Tokyo Green hexanoate, fluorescein di-octanoate, fluorescein di-4-hydroxy-2-nonenoate, fluorescein di-benzoate and fluorescein di-4-diethylaminobenzoate.

According to another embodiment of the present invention, when the ALDH isoenzyme is ALDH9, R and R', which are identical or different, are chosen in order to obtain 4-aminobutyrate.

In particular, when the ALDH isoenzyme is ALDH9, a specific substrate according to the invention is chosen from among resorufin 4-aminobutyrate, 7-hydroxycoumarin 4-aminobutyrate and 2-methyl-4-methoxy-Tokyo Green 4-aminobutyrate, fluorescein di-4-aminobutyrate.

According to one of these aspects, the present invention also relates to a composition comprising at least one specific substrate according to the invention.

The composition according to the invention thus comprises 1, 2, 3, 4, 5, 6, 7, 8, 9, 10, 11, 12, 13, 14, 15, 17, 18, 19 or more specific substrates according to the invention.

This composition thus makes it possible to detect and directly identify several isoenzymes of ALDH. For example, the composition comprises a specific substrate of ADLH1 and a specific substrate for ALDH3, or a specific substrate for ALDH1 and ALDH9, or ALDH3 and ALDH 9, or ALDH1, ALDH3 and ALDH9.

Thus, the composition according to the invention may, for example, comprise one or more of the following specific substrates: resorufin retinoate, resorufine propionate, resorufine octanoate, resorufin benzoate, resorufine 4-aminobutyrate, resorufin hexanoate or resorufin 4-hydroxy-2-nonenoate, resorufin 4-diethylaminobenzoate, 7-hydroxycoumarin retinoate, 7-hydroxycoumarin propionate, 7-hydroxycoumarin octanoate, 7-hydroxycoumarin benzoate, 7-hydroxycoumarin 4-aminobutyrate, 7-hydroxycoumarin hexanoate or 7-hydroxycoumarine 4-hydroxy-2-nonenoate, 7-hydroxycoumarine 4-diethylaminobenzoate, 2-methyl-4-methoxy Tokyo Green, 2-methyl-4-methoxy-Tokyo Green propionate, 2-methyl-4-methoxy-Tokyo Green octanoate, 2-methyl-4-methoxy-Tokyo Green benzoate, 2-methyl-4-methoxy-Tokyo Green 4-aminobutyrate, 2-methyl-4-methoxy-Tokyo Green hexanoate or 2-methyl-4-methoxy-Tokyo Green 4-hydroxy-2-nonenoate, 2-methyl-4-methoxy-Tokyo Green 4-diethylaminobenzoate, fluorescein di-retinoate, fluorescein dipropionate, fluorescein di-octanoate, fluorescein di-benzoate, fluorescein di-4-aminobutyrate, fluorescein di-hexanoate or fluorescein di-4-hydroxy-2-nonenoate, fluorescein di-4-diethylaminobenzoate.

In particular, the specific substrate according to the invention is characterized in that the ALDH isoenzyme is detected in a cell population.

By "cell population" is meant a set of cells of the same or different origin and whose characteristics (genetic sequences, levels of expression, state of differentiation) are identical or different. In particular, the cell population comprises at least 2 cells, for example 10, 100, 1000 or 1000000 cells.

Thus, according to one embodiment of the present invention, the specific substrate is detected in vitro or ex vivo by the use of the fluorescence plate technique, the flow cytometry technique and/or the immunofluorescence technique.

The specific substrates according to the invention are useful for identifying the different ALDH isoenzymes. They make it possible, in particular, to identify cells expressing the different ALDH isoenzymes (for example, certain types of stem cells) and to distinguish them in a mixed population from those which do not express an ALDH isoenzyme or not the same ALDH isoenzyme. The substrates according to the invention may also make it possible to distinguish cells which express an ALDH isoenzyme to a greater degree than the cells which express it to a lesser degree.

Thus, the present invention relates to the use of at least one specific substrate according to the invention for quantifying at least one ALDH isoenzyme in a cell population.

Thus, the present invention also relates to the use of at least one specific substrate according to the invention for isolating and/or selecting a part of a cell population overexpressing an ALDH isoenzyme.

Thus, the present invention also relates to the use of at least one specific substrate according to the invention for sorting all or part of a cell population according to its expression of at least one ALDH isoenzyme.

"At least one" ALDH isoenzyme is defined as 1, 2, 3, 4, 5, 6, 7, 8, 9, 10, 11, 12, 13, 14, 15, 17, 18 or 19 ALDH isoenzymes. The 19 isoenzymes have been described previously.

"At least one" specific substrate according to the invention has the same meaning as previously described.

The present invention also relates to a method for quantifying at least one ALDH isoenzyme in a cell population, comprising the use of at least one specific substrate according to the invention.

Quantification may be performed using a fluorescence plate technique. The identification and/or quantification of the different isoenzymes of ALDH makes it possible to distinguish and/or identify different cell types.

Thus, the present invention also relates to the use of at least one specific substrate according to the invention for distinguishing healthy stem cells from cancer stem cells.

It also relates to a method for distinguishing healthy stem cells from cancer stem cells comprising the use of at least one specific substrate according to the invention.

The method and the use also make it possible to isolate these cells, for example by including a step of isolating the cells having a fluorescence.

For example, "cancer stem cells" means stem cells of cancer of the bladder, breast, cervix, colon, head and neck, liver, lung, pancreas, prostate, ovarian, leukemia.

In particular, the specific substrate according to the invention is used to distinguish the stem cells from solid cancers and/or hematological malignant tumors.

For example, "solid cancer" means breast, lung or prostate cancer.

By "hematological malignancies" is meant, for example, leukemia, lymphoma or myeloma.

In particular, the stem cells of interest are cancerous or healthy hematopoietic cells. The identification and/or quantification of the different ALDH isoenzymes also makes it possible to characterize different stages of a disease or cell differentiation.

Thus, the present invention also relates to the use of at least one specific substrate according to the invention for characterizing the various stages of a cancer or the different stages of stem cell differentiation.

It also relates to a method for characterizing the various stages of a cancer or the different stages of stem cell differentiation comprising the use of at least one specific substrate according to the invention.

By "different stages of the differentiation of stem cells" is meant the stages which are well known to those skilled in the art, in particular the following stages: undifferentiated cells, poorly differentiated cells, moderately differentiated cells, and well differentiated cells.

By "different stages of a cancer" are meant the stages which are well known to those skilled in the art, in particular the following stages: tumor or undifferentiated cancer, tumor or poorly differentiated cancer, tumor or moderately differentiated cancer, tumor or well differentiated cancer.

The specific substrates according to the invention are useful as a diagnostic marker by allowing the identification and/or quantification of the different ALDH isoenzymes.

The present invention therefore also relates to a diagnostic marker comprising a specific substrate according to the invention.

By "diagnostic marker" is meant the meaning commonly attributed to these terms by those skilled in the art, i.e. a characteristic element making it possible to confirm or invalidate a diagnosis.

According to one embodiment of the present invention, the diagnostic marker according to the invention is a specific substrate according to the invention.

Thus, the present invention also relates to the use of a marker according to the invention for the diagnosis of a disease involving deregulation of an ALDH isoenzyme.

It also relates to a method for diagnosing a disease involving deregulation of an ALDH isoenzyme comprising the use of a marker according to the invention.

A disease involving deregulation of an ALDH isoenzyme is a disease implying that the isoenzyme will be overexpressed or under-expressed in the patient in relation to the so-called normal expression, i.e. the expression observed in a healthy subject.

By "overexpressed" or "overexpression" is meant an expression rate in the sick subject that is greater than that of the healthy subject.

By "under expressed" or "under expression" means an expression rate in the patient that is less than that of the healthy subject.

Such a disease may be selected from cancers, disorders of sperm motility, ischemia, head trauma or pancreatitis.

By "cancer" is meant, for example, leukemia, breast cancer or lung cancer.

"Sperm motility disorders" means disorders affecting the rate at which sperm can move and pass through the woman's cervix, uterus and fallopian tubes.

The present invention also relates to the use of a marker according to the invention for determining whether a subject is capable of responding to a therapy that inhibits the activity of an ALDH isoenzyme and/or is directed against cancer stem cells.

It also relates to a method for determining whether a subject is capable of responding to a therapy that inhibits the activity of an ALDH isoenzyme and/or is directed against cancer stem cells comprising the use of a marker according to the invention.

In the context of the present invention, "subject" refers to a warm-blooded animal such as a mammal, animal or human, in particular a human being. The subject may be a healthy subject or a subject suffering from, or having the potential to be afflicted by, one or more diseases and/or conditions described within the scope of the present invention.

By "therapy inhibiting the activity of an ALDH isoenzyme" is meant a therapy whose direct or indirect target is an ALDH isoenzyme such as, for example, ALDH1, ALDH3, ALDH9 or several ALDH isoenzymes.

By "therapy directed against cancer stem cells" is meant a therapy whose target would be cancer stem cells, one of the characteristics of which is the high level of ALDH.

According to one of these aspects, the present invention also relates to a method for distinguishing cells expressing at least one ALDH isoenzyme in a cell population, wherein the method comprises:
  (a) bringing the cell population into contact with at least one specific substrate according to the invention,
  (b) measuring the fluorescence of the cell population; and
  (c) identifying cells with increased fluorescence relative to the fluorescence of the cell population before the population is brought into contact with the at least one specific substrate.

By "bringing into contact" is meant, in particular, the incubation with at least one specific substrate according to the invention for a defined time ranging from a few minutes, for example 30 minutes, to several hours, for example 4 hours or more, with the cell population.

A "cell population" is as defined above. "At least one ALDH isoenzyme" and "at least one specific substrate according to the invention" are as defined above.

The measurement of the fluorescence may be carried out by any method known to those skilled in the art. By way of example, mention may be made of the use of the fluorimeter, the flow cytometer or fluorescence microscopy.

By "an increased fluorescence relative to the fluorescence of the cell population before the population is brought into contact with the specific substrate", is meant a florescence of the studied cell population greater than the fluorescence of this same cell population before it has been brought into contact with the specific substrate according to the invention.

If at least two specific substrates for at least two different ALDH isoenzymes are brought into contact with the cell population, the method may also include an additional step d) comprising distinguishing between cells expressing the at least two ALDH isoenzymes of the cell.

This distinction may, for example, be made by observing different fluorescence colors depending on the isoenzyme detected.

For example, if the method involves contacting the cell population with resorufin retinoate and 7-hydroxycoumarin octanoate, cells with increased red fluorescence will be identified as expressing ALDH1, while cells with increased blue fluorescence will be identified as expressing ALDH3.

According to one of these aspects, the present invention also relates to a kit for the various uses mentioned in the context of the present invention, in particular for quantifying an ALDH isoenzyme, more particularly in a cell population comprising at least one specific substrate according to the invention.

The kit may also be a kit for the diagnosis of a disease involving deregulation of an ALDH isoenzyme, wherein the disease is chosen, for example, from: cancers, disorders of sperm motility, ischemia, head trauma or pancreatitis, in order to determine whether a subject is capable of responding to therapy that inhibits the activity of an ALDH isoenzyme and/or is directed against cancer stem cells in order to distinguish healthy stem cells from cancer stem cells, for example to distinguish stem cells from solid cancers and/or hematological malignancies; or to characterize the different stages of a cancer or the different stages of stem cell differentiation.

The kits according to the invention may, for example, also comprise instructions for the use of the kit for determining the quantity of an ALDH isoenzyme, in particular in a cell population, for the diagnosis of a disease involving deregulation of an ALDH isoenzyme, to determine whether a subject is capable of responding to therapy that inhibits the activity of an ALDH isoenzyme and/or is directed against cancer stem cells, to distinguish healthy cancer stem cells, or to characterize the different stages of a cancer, or the different stages of stem cell differentiation.

The various compounds included in a kit according to the invention may be provided in the form of a solid (for example freeze-dried) or in liquid form.

Kits of the present invention may optionally include different containers (e.g. ampule, test tube, vial or bottle) for each compound. Each compound will usually be aliquoted in its container or provided in a concentrated form. Other suitable containers for carrying out certain steps of the methods described in the context of the present invention may also be provided.

BRIEF DESCRIPTION OF THE DRAWINGS

The present invention will be further illustrated by the following figures and examples.

DETAILED DESCRIPTION

Examples

Figure 1:
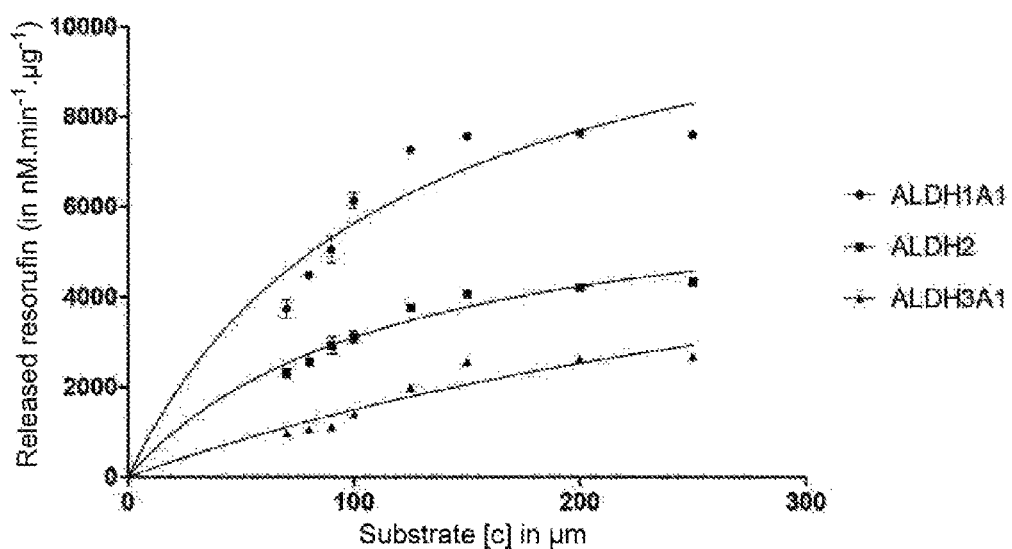
FIG. 1: Michaelis-Menten plot to determine the $K_m$ and $V_{max}$ of resorufine propionate on ALDH1A1, ALDH2 and ALDH3A1.

1. Preparation of Specific Substrates According to the Invention

Operating Conditions

Commercial reagents and solvents (Fisher, Sigma, Fluorochem, etc.) were used without purification except for dichloromethane distilled under an inert atmosphere on $CaH_2$. The reactions were monitored by thin layer chromatography on aluminum sheets coated with Macherey-Nagel silica gel ALUGRAM SIL G/UV$_{254}$ (thickness 0.2 mm), the observation of the plates was carried out under a 254 and 312 nm ultraviolet lamp.

The column chromatographies were carried out on Macherey-Nagel silica gel 60M (40-63 µm) under air pressure.

Melting points were measured with a Tottoli Büchi SMP-20 instrument and were not corrected.

$^1$H NMR spectra were recorded with Brucker ALS300 or DRX300 300 MHz devices. The $^{13}$C NMR spectra were obtained on Brucker DRX300 75 MHz devices. The chemical shifts δ are expressed in parts per million (ppm), the residual peak of the solvent having been taken as the internal reference. The coupling constants J are expressed in Hz.

Mass spectra were recorded in positive mode on a hybrid time-of-flight mass spectrometer (MicroTOFQ-II, Bruker Daltonics, Bremen) with an electrospray source (ESI).

The spray gas flow was at 0.4 bar and the capillary voltage at 3500 v. The solutions were perfused at 10 µl/min in a solvent mixture (methanol/dichloromethane/water 45/40/15) with 1% formic acid. The mass range of the assay was 50-1000 m-z and calibration was performed with sodium formate.

Structural Examples of Specific Substrates According to the Invention

TABLE 3

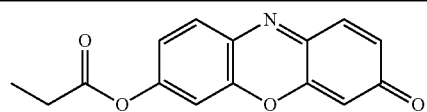

Resorufine propionate

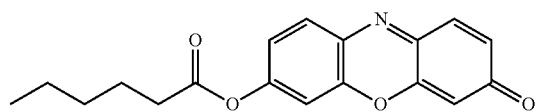 [SMILES: CCCCCC(=O)Oc1ccc2nc3ccc(=O)cc-3oc2c1]

Resorufin hexanoate

TABLE 3-continued

| Structure | Name |
|---|---|
| 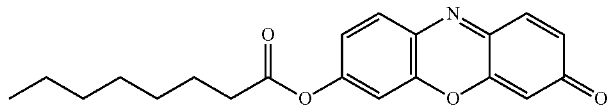 [SMILES: CCCCCCCC(=O)Oc1ccc2nc3ccc(=O)cc-3oc2c1] | Resorufin octanoate |
| 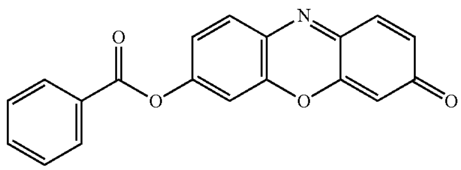 [SMILES: O=C(Oc1ccc2nc3ccc(=O)cc-3oc2c1)c1ccccc1] | Resorufine benzoate |
| 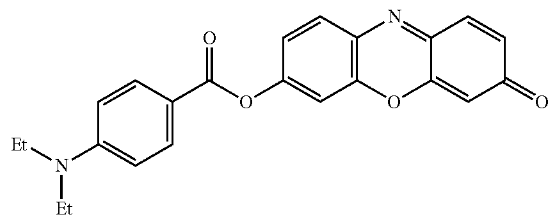 [SMILES: CCN(CC)c1ccc(C(=O)Oc2ccc3nc4ccc(=O)cc-4oc3c2)cc1] | Resorufin 4-diethylaminobenzoate |
| 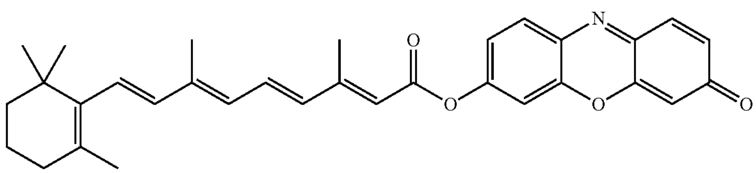 [SMILES: CC1=C(/C=C/C(C)=C/C=C/C(C)=C/C(=O)Oc2ccc3nc4ccc(=O)cc-4oc3c2)C(C)(C)CCC1] | Resorufine retinoate |
| 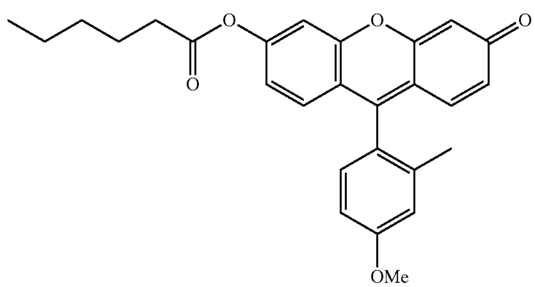 [SMILES: CCCCCC(=O)Oc1ccc2c(-c3ccc(OC)cc3C)c3ccc(=O)cc-3oc2c1] | 2-Methyl-4-methoxy-Tokyo Green hexanoate |
| 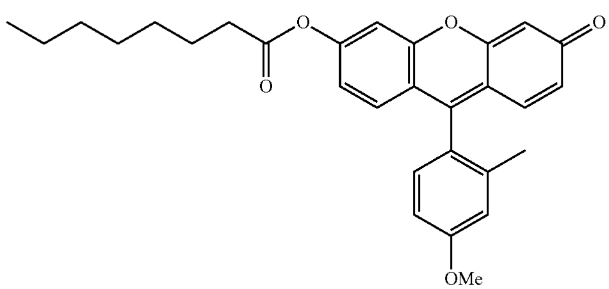 [SMILES: CCCCCCCC(=O)Oc1ccc2c(-c3ccc(OC)cc3C)c3ccc(=O)cc-3oc2c1] | 2-Methyl-4-methoxy-Tokyo Green octanoate |
| 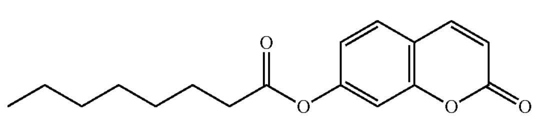 [SMILES: CCCCCCCC(=O)Oc1ccc2ccc(=O)oc2c1] | 4-hydroxycoumarin octanoate |
| 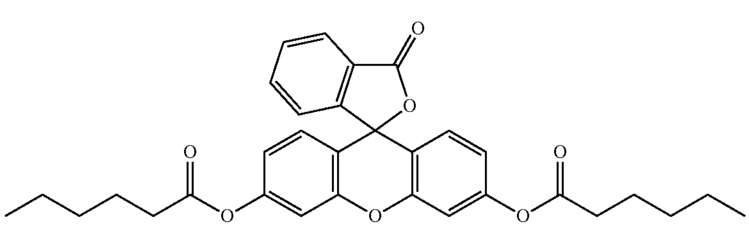 [SMILES: CCCCCC(=O)Oc1ccc2c(c1)Oc1cc(OC(=O)CCCCC)ccc1C21OC(=O)c2ccccc21] | Fluorescein di-hexanoate |

TABLE 3-continued

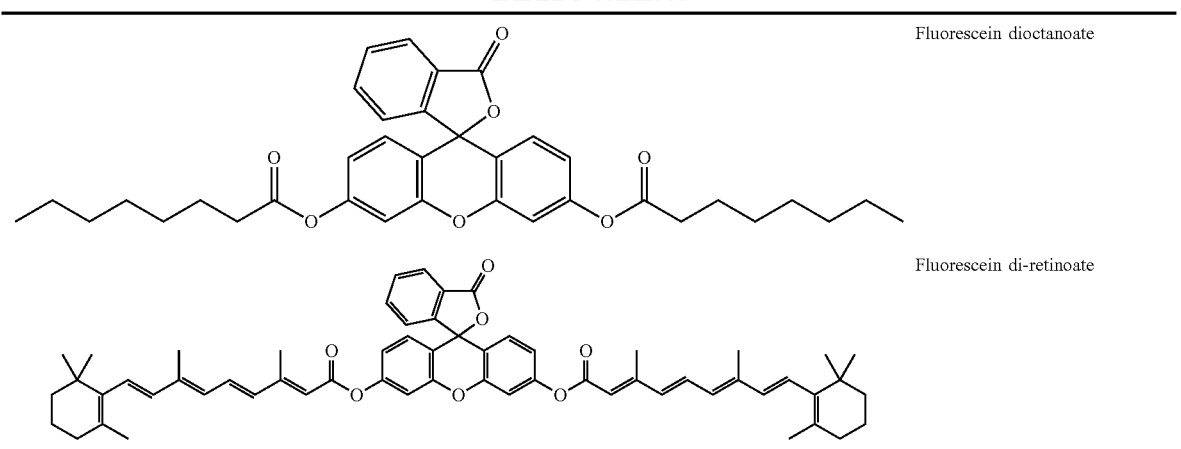

Fluorescein dioctanoate

Fluorescein di-retinoate

Resorufin Esters

Resorufin Propionate and Benzoate

The compounds were prepared from resorufin (sodium salt) (Sigma) with the corresponding acid chloride (2 equivalents) in dichloromethane (0.05M) in the presence of DIPEA (diisopropylethylamine, 2 equivalents).

For proprionate, a suspension of resorufin sodium salt (235.2 mg, 1.0 mmol) in 20 mL of anhydrous DCM was added DIPEA (2 equivalents) at room temperature and then propionyl chloride (2 equivalents) dropwise at 0° C. After 5 minutes at 0° C., the reaction medium was brought to room temperature and stirred overnight. 30 mL of water was then added and extraction with 3×30 mL of DCM was performed. The combined organic phases were washed with 30 ml of a saturated solution of $NaHCO_3$ and then 30 ml of a saturated solution of NaCl. After drying over $Na_2SO_4$, filtration and evaporation of the solvent, the residue was taken up in EtOH. Sonication was performed and the solid obtained was sintered and washed with EtOH (twice). After drying under vacuum 218 mg (81%) of an orange solid were obtained.

Mp 176-177° C. (EtOH) (Guilbault et al Analytical Chem 1965, 37, 120-123:177° C.); [1]HRMN (300 MHz, DMSO) δ 7.89 (d, J=8.7 Hz, 1H), 7.57 (d, J=9.8 Hz, 1H), 7.40 (d, J=2.3 Hz, 1H), 7.25 (dd, J=8.7, 2.4 Hz, 1H), 6.84 (dd, J=9.8, 2.0 Hz, 1H), 6.31 (d, J=2.0 Hz, 1H), 2.66 (q, J=7.4 Hz, 2H), 1.15 (t, J=7.5 Hz, 3H); ESI-MS m/z 270.1 [M+H]+.

Weight: 269.2 g·mol$^{-1}$.
Formula: $C_{15}H_{11}NO_4$

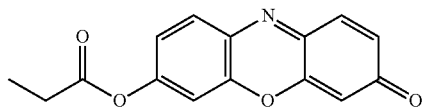 [SMILES: CCC(=O)Oc1ccc2nc3ccc(=O)cc-3oc2c1]

For benzoate, the procedure is identical to that of propionate. Benzoyl chloride was used (scale: 1.0 mmol). The isolated solid (166 mg) was purified by silica gel chromatography (MeOH/DCM: 1/99) to give 156 mg (49%) of pure benzoate.

Mp>210° C. (Guilbault et al Analytical Chem 1965, 37, 120-123: 203° C.); [1]HRMN (300 MHz, DMSO) δ 8.21-8.14 (m, 2H), 7.95 (d, J=8.7 Hz, 1H), 7.84-7.75 (m, 1H), 7.62 (ddd, J=11.7, 10.5, 8.1 Hz, 4H), 7.44 (dd, J=8.7, 2.4 Hz, 1H), 6.86 (dd, J=9.8, 2.1 Hz, 1H), 6.33 (d, J=2.1 Hz, 1H); ESI-MS m/z 318.1 [M+H]+.

Weight: 317.3 g·mol$^{-1}$
Formula: $C_{19}H_{11}NO_4$

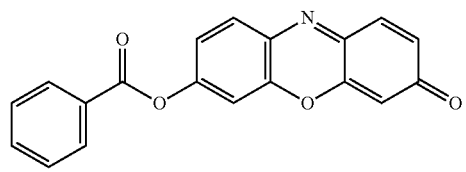 [SMILES: O=C(Oc1ccc2nc3ccc(=O)cc-3oc2c1)c1ccccc1]

Resorufin Hexanoate and Octanoate

The compounds were prepared and isolated in the same manner as for the two preceding esters using the corresponding acid chlorides. The respective yields obtained are 65% and 81%.

For hexanoate, the procedure is identical to that of propionate. Hexanoyl chloride (scale: 1.0 mmol) was used. The compound obtained was isolated by precipitation in EtOH, followed by 2 washes with EtOH, yield 65%.

$^Mp$ 130-132° C.; [1]HRMN (300 MHz, DMSO) δ 7.89 (d, J=8.7 Hz, 1H), 7.57 (d, J=9.8 Hz, 1H), 7.39 (d, J=2.3 Hz, 1H), 7.24 (dd, J=8.7, 2.4 Hz, 1H), 6.84 (dd, J=9.8, 2.0 Hz, 1H), 6.30 (d, J=2.0 Hz, 1H), 2.63 (t, J=7.4 Hz, 2H), 1.75-1.57 (m, 2H), 1.43-1.25 (m, 4H), 0.90 (t, J=7.0 Hz, 3H); ESI-MS m/z312.1 [M+H]+.

Weight: 311.3 g·mol$^{-1}$
Formula: $C_{18}H_{17}NO_4$

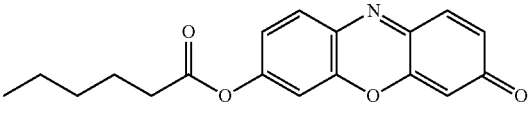 [SMILES: CCCCCC(=O)Oc1ccc2nc3ccc(=O)cc-3oc2c1]

For octanoate, the procedure is identical to that of propionate. Octanoyl chloride (scale: 1.0 mmol) was used. The compound obtained was isolated by precipitation in EtOH, followed by 2 washes with EtOH, yield 81%.

Mp 127-129° C.; [1]HRMN (300 MHz, DMSO) δ 7.89 (d, J=8.7 Hz, 1H), 7.57 (d, J=9.8 Hz, 1H), 7.39 (d, J=2.4 Hz,

1H), 7.23 (dd, J=8.7, 2.4 Hz, 1H), 6.84 (dd, J=9.8, 2.0 Hz, 1H), 6.30 (d, J=2.1 Hz, 1H), 2.63 (t, J=7.4 Hz, 2H), 1.72-1.57 (m, 2H), 1.44-1.19 (m, 8H), 0.87 (t, J=6.8 Hz, 3H); ESI-MS m/z 340.2 [M+H]+.

Weight: 339.4 g·mol$^{-1}$

Formula: $C_{20}H_{21}NO_4$

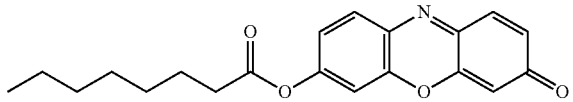 [SMILES: CCCCCCCC(=O)Oc1ccc2nc3ccc(=O)cc-3oc2c1]

Resorufin 4-diethylamino benzoate

The sodium salt of resorufin (235.2 mg, 1.0 mmol), 4-diethylaminobenzoic acid (1.1 equivalent), EDCI (1.1 equivalent) and 4-DMAP (0.1 equivalent) were placed under argon. 25 ml of DCM were added and the reaction medium was stirred overnight at room temperature. The solvent was evaporated and the residue purified by chromatography on silica gel (MeOH/DCM=1/99 to 2.5/87.5) to give 207 mg (53%) of product with a very slight impurity (visible UV) that the second column (MeOH/DCM=1/99) allows to eliminate. $^1$HRMN (300 MHz, DMSO) δ 7.92 (d, J=9.0 Hz, 3H), 7.59 (d, J=9.8 Hz, 1H), 7.49 (s, 1H), 7.35 (d, J=8.5 Hz, 1H), 6.85 (d, J=9.6 Hz, 1H), 6.79 (d, J=9.2 Hz, 2H), 6.32 (d, J=2.0 Hz, 1H), 3.46 (q, J=7.0 Hz, 4H), 1.14 (t, J=7.0 Hz, 6H); ESI-MS m/z 389.1 [M+H]+.

Weight: 388.4 g·mol$^{-1}$

Formula: $C_{23}H_{20}N_2O_4$

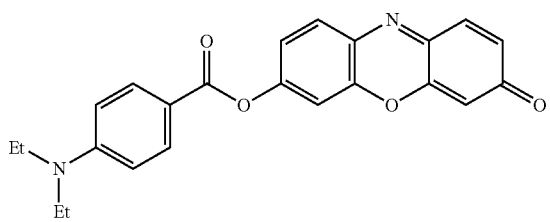 [SMILES: CCN(CC)c1ccc(C(=O)Oc2ccc3nc4ccc(=O)cc-4oc3c2)cc1]

(All) Trans Retinoate of Resorufin

The compound was prepared in the same manner as the preceding ester using commercial retinoic acid (40% yield). The crude (orange-red solid) obtained was washed with MeOH and purified by chromatography on silica gel (MeOH/DCM: 1/99). Further washing with EtOH then MeOH gave 100 mg (40%) of pure product. Mp 150-160 (decomposition); $^1$HRMN (300 MHz, CDCl$_3$) δ 7.82 (d, J=8.6 Hz, 1H), 7.46 (d, J=9.8 Hz, 1H), 7.25-7.10 (m, 3H), 6.89 (dd, J=9.8, 2.0 Hz, 1H), 6.46-6.31 (m, 3H), 6.26-6.14 (m, 2H), 6.00 (s, 1H), 2.45 (d, J=0.9 Hz, 3H), 2.10-2.00 (m, 5H), 1.75 (d, J=0.6 Hz, 3H), 1.70-1.58 (m, 2H), 1.54-1.46 (m, 2H), 1.06 (s, 6H); ESI-MS m/z 496.2 [M+H+].

Weight: 495.6 g·mol$^{-1}$

Formula: $C_{32}H_{33}NO_4$

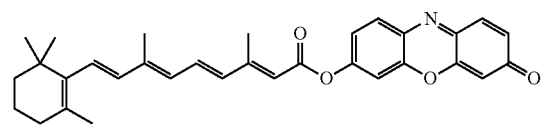 [SMILES: CC1=C(/C=C/C(C)=C/C=C/C(C)=C/C(=O)Oc2ccc3nc4ccc(=O)cc-4oc3c2)C(C)(C)CCC1]

Tokyo-Green Esters

2-Me-4-MeO tokyo-green (CAS No. 643755-84-4: 6-hydroxy-9-(4-methoxy-2-methylphenyl)-3H-Xanthen-3-one) was synthesized in two steps: a bis-silylation of the commercial 3,6-dihydroxyxanth-9-one carried out according to the procedure described in the article "J. Biol. Chem Vol. 264, No. 14. Issue of May 15, PP. 8171-8178, 1989" led to 3,6-bis (t-butyldimethylsilyloxy) xanthone. A second step carried out according to the procedure described in the article "Chem. Eur. J. 2014, 20, 447-455" consisting of treatment with magnesium from 2-bromo-3-methoxytoluene followed by acid hydrolysis gave 2-Me-4-MeO tokyo green.

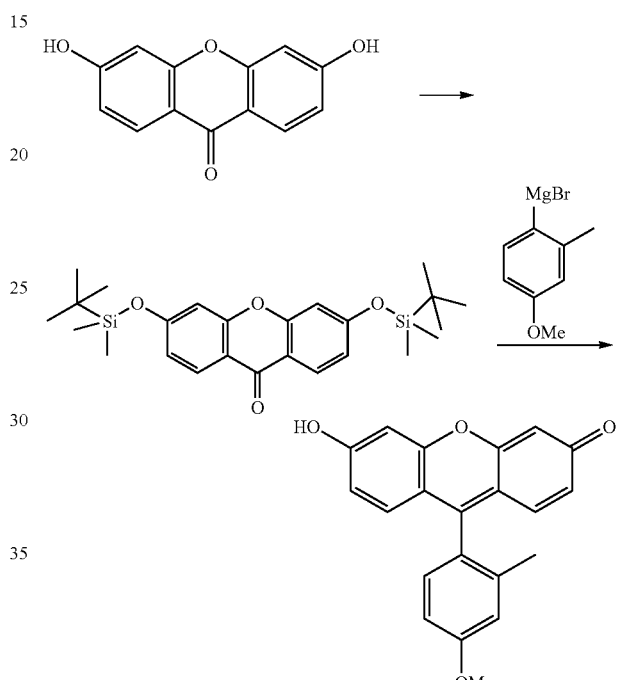

Hexanoate and Octanoate of 2-Me-4-MeO Tokyo-Green

The compounds were prepared conventionally using the corresponding acid chlorides.

For hexanoate, from 0.15 mmol of 2-Me-4-MeO-TG, purification by chromatography on silica gel (MeOH/DCM: 1/99 to 10/90) was carried out, yield: 40% (non-crystallized resin).

$^1$HRMN (300 MHz, MeOD) et 7.45 (d, J=2.0 Hz, 1H), 7.24 (d, J=8.8 Hz, 1H), 7.16 (d, J=9.6 Hz, 2H), 7.11 (dd, J=8.8, 2.1 Hz, 1H), 7.04 (d, J=2.1 Hz, 1H), 6.99 (dd, J=8.4, 2.3 Hz, 1H), 6.61 (dd, J=9.7, 1.9 Hz, 1H), 6.44 (d, J=1.9 Hz, 1H), 3.89 (s, 3H), 2.63 (t, J=7.4 Hz, 2H), 2.04 (s, 3H), 1.81-1.67 (m, 2H), 1.47-1.33 (m, 4H), 1.00-0.89 (m, 3H).

$^{13}$CRMN (101 MHz, CDCl3) et 186.23, 171.64, 160.63, 158.85, 154.54, 153.29, 148.87, 138.07, 131.00, 130.88, 130.58, 129.38, 124.29, 120.84, 118.85, 118.56, 116.24, 111.80, 110.38, 106.18, 77.16, 55.51, 34.47, 31.32, 24.60, 22.42, 20.19, 14.05;

ESI-MS: [M+H]+: 431.1

Weight: 430.5 g·mol$^{-1}$

Formula: $C_{27}H_{26}O_5$

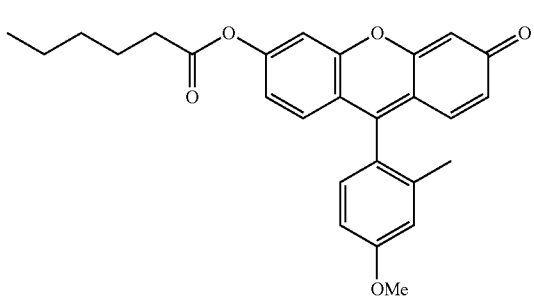 [SMILES: CCCCCC(=O)Oc1ccc2c(-c3ccc(OC)cc3C)c3ccc(=O)cc-3oc2c1]

For the octanoate, from 0.19 mmol of TG, purification by chromatography on silica gel (MeOH/DCM: 1/99 to 10/90), was carried out, yield: 20% (non-crystallized resin)

¹H RMN (300 MHz, MeOD) et 7.46 (s, 1H), 7.25 (d, J=8.8 Hz, 1H), 7.17 (d, 1=8.9 Hz, 2H), 7.12 (dd, J=8.8, 1.6 Hz, 1H), 7.05 (d, J=2.1 Hz, 1H), 7.00 (cid, 1=8.4, 2.2 Hz, 1H), 6.62 (dd, J=9.7, 1.5 Hz, 1H), 6.45 (s, 1H), 3.90 (s, 3H), 2.64 (t, J=7.4 Hz, 2H), 2.05 (s, 3H), 1.81-1.67 (m, 2H), 1.49-1.26 (m, 9H), 0.96-0.87 (m. 3H).

¹³CRMN (101 MHz, CDCl3) et 186.20, 171.66, 160.61, 158.78, 154.49, 130.92, 130.59, 129.34, 124.33, 120.89, 118.86, 106.23, 77.16, 55.51, 34.51, 31.76, 29.14, 29.02, 24.92, 22.73, 20.19, 14.21.

ESI-MS: [M+H]+: 459.2

Weight: 485 g·mol⁻¹

Formula: $C_{29}H_{30}O_5$

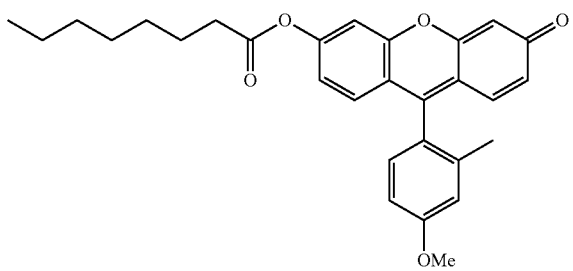 [SMILES: CCCCCCCC(=O)Oc1ccc2c(-c3ccc(OC)cc3C)c3ccc(=O)cc-3oc2c1]

Fluorescein Diesters

The identical preparation is as described above using 3.0 eq. corresponding acid chlorides and 3 eq. basic. Hexanoate and octanoate have already been described [litt. Ge, Feng-Yan; *Dyes and Pigments* 2007, 72 (3), 322-326].

Fluorescein Di-Hexanoate

[7364-90-1] Scale 0.8 mmol, purification by chromatography on silica gel (PE/EtOAc: 90/10). White solid, yield: 98%. Mp 103-105° C. (pentane washings) (100° C., Ge, Feng-Yan, *Dyes and Pigments* 2007, 72 (3), 322-326);

¹H NMR (300 MHz, DMSO) δ 8.09-8.03 (m, 1H), 7.83 (td, J=7.4, 1.4 Hz, 1H), 7.77 (td, J=7.4, 1.2 Hz, 1H), 7.44-7.38 (m, 1H), 7.28 (d, J=2.0 Hz, 2H), 6.94 (dd, J=8.7, 2.2 Hz, 2H), 6.88 (d, J=8.6 Hz, 2H), 2.60 (t, J=7.4 Hz, 4H), 1.71-1.58 (m, 4H), 1.40-1.25 (m, 8H), 0.95-0.81 (m, 6H);

ESI-MS: [M+H]+: 529.2

Weight: 528.9 g·mol⁻¹

Formula: $C_{32}H_{32}O_7$

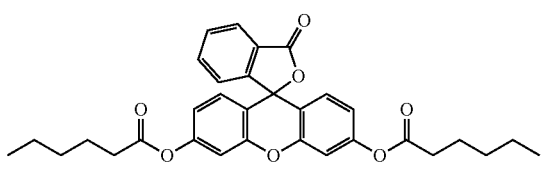 [SMILES: CCCCCC(=O)Oc1ccc2c(c1)Oc1cc(OC(=O)CCCCC)ccc1C21OC(=O)c2ccccc21]

Fluorescein Dioctanoate

[19722-86-2] Scale 0.8 mmol, purification by chromatography on silica gel (PE/EtOAc: 90/10 to 80/20). White solid, 92%. Mp 50-52°. (lit 49° C., Ge, Feng-Yan, *Dyes and Pigments* 2007, 72 (3), 322-326).

¹H NMR (300 MHz, DMSO) δ 8.09-8.04 (m, 1H), 7.83 (td, J=7.4, 1.3 Hz, 1H), 7.77 (td, J=7.3, 1.0 Hz, 1H), 7.41 (d, J=7.3 Hz, 1H), 7.27 (d, J=2.1 Hz, 2H), 6.94 (dd, J=8.7, 2.2 Hz, 2H), 6.88 (d, J=8.6 Hz, 2H), 2.59 (t, J=7.4 Hz, 4H), 1.70-1.57 (m, 4H), 1.41-1.20 (m, 16H), 0.92-0.81 (m, 6H);

ESI-MS: [M+H]+: 585.3.

Weight: 584.7 g·mol⁻¹

Formula: $C_{36}H_{40}O_7$

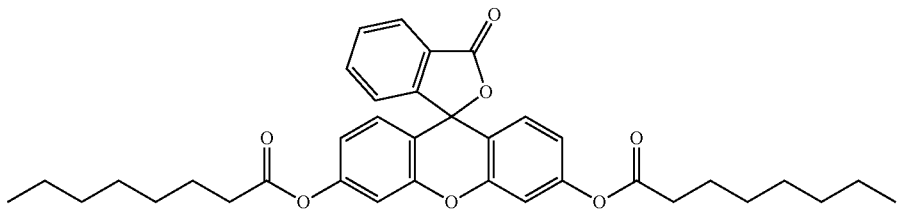 [SMILES: CCCCCCCC(=O)Oc1ccc2c(c1)Oc1cc(OC(=O)CCCCCCC)ccc1C21OC(=O)c2ccccc21]

Fluorescein Di-Retinoate

The compound was prepared from 2.1 equivalents of retinoic acid, 2.1 equivalents of EDCI, 0.1 equivalents of 4-DMAP. Scale: 0.5 mmol, purification by chromatography on silica gel (PE/EtOAc: 80/20). Yellow solid, 45% yield. M.p. 145-150° C. (dec);

¹H NMR (300 MHz, DMSO) δ 8.07 (d, J=7.3 Hz, 1H), 7.89-7.73 (m, 2H), 7.42 (d, J=7.3 Hz, 1H), 7.31 (d, J=2.3 Hz, 1H), 7.20 (dd, J=15.0, 11.5 Hz, 2H), 6.98 (dd, J=8.7, 2.2 Hz, 2H), 6.88 (d, J=8.7 Hz, 2H), 6.54 (d, J=15.0 Hz, 2H), 6.39-6.15 (m, 6H), 6.11 (s, 2H), 2.38 (s, 6H), 2.07-1.95 (m, 10H), 1.70 (s, 6H), 1.63-1.51 (m, 4H), 1.50-1.40 (m, 4H), 1.03 (s, 12H).
ESI-MS: [M+H]+: 897.3
Weight: 879.1 g·mol$^{-1}$
Formula: $C_{60}H_{64}O_7$

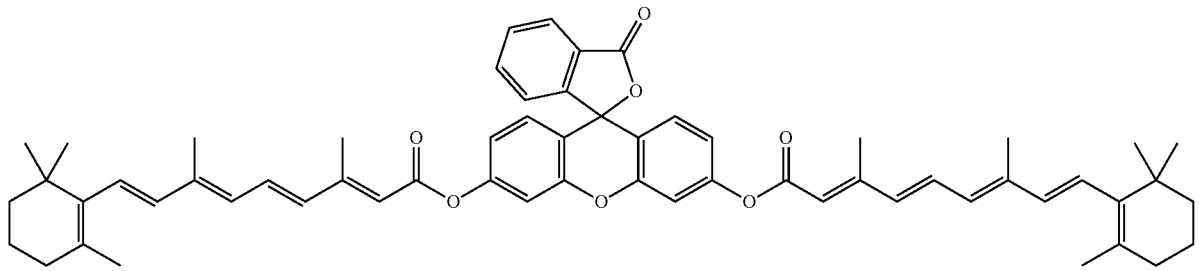 [SMILES: CC1=C(/C=C/C(C)=C/C=C/C(C)=C/C(=O)Oc2ccc3c(c2)Oc2cc(OC(=O)/C=C(C)/C=C/C=C(C)/C=C/C4=C(C)CCCC4(C)C)ccc2C32OC(=O)c3ccccc32)C(C)(C)CCC1]

Esters of 7-hydroxycoumarin

These esters were prepared in the same manner as previously from 7-hydroxycoumarin and acid chloride in the presence of DIPEA.

7-hydroxycoumarin octanoate

Scale 2 mmol, purification by chromatography on silica gel (PE/EtOAc: 70/30) yield: 92%. Mp 58-59° C.;
$^1$H NMR (300 MHz, DMSO) δ 8.08 (d, J=9.3 Hz, 1H), 7.77 (d, J=8.5 Hz, 1H), 7.26 (d, J=2.2 Hz, 1H), 7.15 (dd, J=8.4, 2.2 Hz, 1H), 6.48 (d, J=9.6 Hz, 1H), 2.61 (t, J=7.4 Hz, 2H), 1.65 (s, 2H), 1.42-1.21 (m, 8H), 0.93-0.81 (m, 3H);
ESI-MS: [M+H]+: 289.1
Weight: 288.3 g·mol$^{-1}$
Formula: $C_{17}H_{20}O_4$

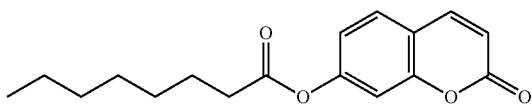 [SMILES: CCCCCCCC(=O)Oc1ccc2ccc(=O)oc2c1]

2. Activity of Specific Substrates According to the Invention

Material and Methods

Cell Lines

NCI-H522 and A549 lung cancer cells as well as leukemia lines were used. The cells were obtained from American Type Culture Collection (ATCC), the European Collection of Cell Cultures (ECACC) and Deutsche Sammlung von Mikroorganismen und Zellkultruren (DSMZ).

Determination of the Km and Vmax of Resorufine Propionate with the Different Isoenzymes ALDH1A1, ALDH2 and ALDH3A1 Purified In 50 µl of 0.1 M phosphate buffer pH6.00; 0.2 M KCl; 2 mM NADP+; 2 mM EDTA, a range of resorufine propionate was made: 250, 200, 150, 125, 100, 90, 80 and 70 µM and 0 µM. 50 µL of recombinant enzyme solution at 2.5 mU/well ALDH1A1 (R&D Sytems, 5869-DH), ALDH2 (abcam, ab87415) and ALDH3A1 (R&D Sytems, 6705-DH) was added. The incubation was carried out for 30 minutes at +37° C. and then the fluorescence reading was made (Em: 590 nm, Ex: 530 nm). The data were then converted to resorufin released (nM·min-1.µg$^{-1}$) and Km and Vmax were calculated using the Michaelis-Menten equation using GraphPad Prism 5.0.

Treatment of Cells with Specific Inhibitors of ADLH1 and 3

In a 96-well plate, the HL-60 cells were inoculated at a concentration of 50.000 cells/well in RPMI-1640 medium without phenol red supplemented with L-Glutamine, Penicillin, Streptomycin and 10% Fetal Calf Serum (FCS) supplemented with dimethyl ampalthioester (DIMATE) a specific inhibitor ALDH 1 and 3, morpholino ampal thiolester (MATE) a specific inhibitor of ALDH3, at concentrations of 8 µM respectively. After incubation for 6 hours, the substrates of the different ALDHs respectively resorufine propionate for ALDH1 and resorufin 4-diethylaminobenzoate for ALDH3, were added to a final concentration of 10 µM and then incubated for one hour at +37° C. The plate was then read using an Appliskan fluorescent plate reader (ex=560 nm, Em=600). The data were expressed in relative fluorescence units produced by an equal number of cells.

Treatment of Cells with Disulfiram (DSF)

In a 96-well plate, the HL-60 cells were inoculated at a concentration of 50.000 cells/well in RPMI-1640 medium without phenol red supplemented with L-Glutamine, Penicillin, Streptomycin and 10% Fetal Calf Serum (FCS) supplemented with disulfiram (DSF), an inhibitor of ALDH activity, at concentrations of 250 nM and 1000 nM. The cells were then incubated for 1 hour. After incubation, substrates of the different ALDHs, resorufin retinoate and fluorescein di-retinoate for ALDH1, and fluorescein benzoate and fluorescein di-benzoate for ALDH 3, were added to a final concentration of 5 µM then incubated for 30 minutes at +37° C. The plate was then read using a SpectraMax® fluorescent plate reader, Molecular Devices (Ex=560 nm, Em=600 nm for resorufin and ex=485 nm, em=535 nm for fluorescein). The data were expressed in relative fluorescence units.

Treatment of Cells with Retinoic Acid

In a 96-well plate, the HL-60 cells were inoculated at a concentration of 50.000 cells/well in RPMI-1640 medium without phenol red supplemented with L-Glutamine, Penicillin, Streptomycin and 10% Fetal Calf Serum (FCS)

supplemented with retinoic acid, known to be an inhibitor of ALDH activity at 1 µM and 10 µM concentrations. The cells were then incubated for 72 hours. After incubation, the substrates of the different ALDHs, resorufine retinoate and fluorescein di-retetinoate for ALDH1, and fluorescein benzene and fluorescein di-benzote for ALDH3, were added to a final concentration of 5 µM then incubated for 30 minutes at +37° C. The plate was then read using a SpectraMax® fluorescent plate reader, Molecular Devices (Ex=560 nm, Em=600 nm for resorufin and Ex=485 nm, Em=535 nm for fluorescein). The data were expressed in relative fluorescence units.

Treatment of Cells with Interfering RNA ALDH1A1

In a 60 mm Petri dish, the NCI-H522 cells were seeded at a concentration of 250.000 cells/plate, corresponding to a confluence of 40-50%, in RPMI-1640 medium supplemented with L-Glutamine, Penicillin, Streptomycin and 10% Fetal Calf Serum (FCS) overnight at 37° C. The next day, the medium was replaced by the same medium without FCS. The transfection solution was then prepared by diluting 100 nM in 500 µL of culture medium without FCS, to which 500 µL of culture medium without FCS supplemented with 3 µL of lipofectamine 2000 (Invitrogen) was added. The solution was then incubated for 30 minutes at room temperature and then drops added to the cell solution. The mixture was incubated at +37° C. in a 5% $CO_2$ incubator for 8 hours. After the incubation, the medium was changed by medium supplemented with FCS and the cells were left in culture for 48 hours. The inhibition of the protein was validated by Western Blot. The specific activity of ALDH1A1 was then assayed by fluorescence.

Determination of ALDH1 Activity by Resorufine Propionate

The cells were inoculated at a concentration of $1 \times 10^4$ cells/well in a 96-well plate in 100 µl in RPMI-1640 medium without phenol red supplemented with L-Glutamine, Penicillin, Streptomycin and 10% Fetal Calf Serum (FCS) supplemented with 10 µM resorufin propionate. The cells were then incubated for 1 hour and then the plate was read using an Appliskan fluorescent plate reader (ex=560 nm, Em=600). The data were expressed in relative fluorescence units produced by an equal number of cells.

Double Localization of Resorufin Propionate and ALDH1A1 by Fluorescent Microscopy In a 24-well plate with microscope glasses previously washed with ethanol and then placed in the wells, the NCI-H522 cells were added at a cell concentration of 50.000 cells/well and then incubated in RPMI-1640 medium supplemented with L-Glutamine, Penicillin, Streptomycin and 10% Fetal Calf Serum overnight at +37° C. with a 5% $CO_2$ atmosphere. The next day, the culture medium was changed with either DIMATE (5 µM) or the treatment vehicle and incubated for 6 hours. The cells were incubated for 30 minutes with culture medium supplemented with 10 µM of resorufin propionate, were then washed with cold PBS and then fixed with paraformaldehyde for 15 minutes at 37° C. The cells were permeabilized and saturated with PBS; 3% bovine albumin; 0.3% triton for 1 hour. The incubation was carried out with the anti-ALDH1A1 antibody (R&D System, MAB5869) for 1 hour at +37° C., then with an anti-mouse antibody coupled to fluorescein for 1 hour at room temperature in the dark, with PBS washes between the two steps. 3 washes with PBS were carried out then the microscopy glasses were mounted with an anti-decoloration support supplemented with DAPI. The cells were then observed under a microscope.

Identification of Positive ALDH1 Cells by Flow Cytometry

In a 60 mm Petri dish, 500.000 cells were incubated with RPMI-1640 medium supplemented with L-Glutamine, Penicillin, Streptomycin and 10% Fetal Calf Serum overnight at +37° C. with 5% atmosphere. CO2. For the negative control, the cells were taken up in medium supplemented with 15 µM of dimethyl ampal thiolester (Dimate), a specific inhibitor of ALDH1 and 3, then incubated for 5 hours at 37° C., 5% $CO_2$. After trypsination, the cells were taken up in supplemented RPMI medium and centrifuged at 800 g for 5 minutes. The cell pellet was then taken up in fresh supplemented medium containing 10 µM of resorufin propionate, and then incubated for 1 hour in a polycarbonate tube at 37° C., 5% $CO_2$. After incubation, the cells were then centrifuged and then washed in cold PBSx1 and finally taken up in 200 mL of cold PBSx1. The solution was then analyzed by flow cytometry (Ex 590 nm/Em560 nm or red laser).

Results

The results are shown in FIGS. 1 to 5.

In particular, FIG. 1 shows the data obtained to determine the $K_m$ and $V_{max}$ of resorufine propionate. The results are also shown in Table 4 below.

TABLE 4

|  | ALDH1 | ALDH2 | ALDH3 |
|---|---|---|---|
| Vmax | 12132 | 6693 | 8141 |
| Km | 115.5 | 116.0 | 445.1 |
| Km/Vmax | 105.04 | 57.69 | 18.29 |
| Increase | 1 | 0.54 | 0.17 |

Figure 2:
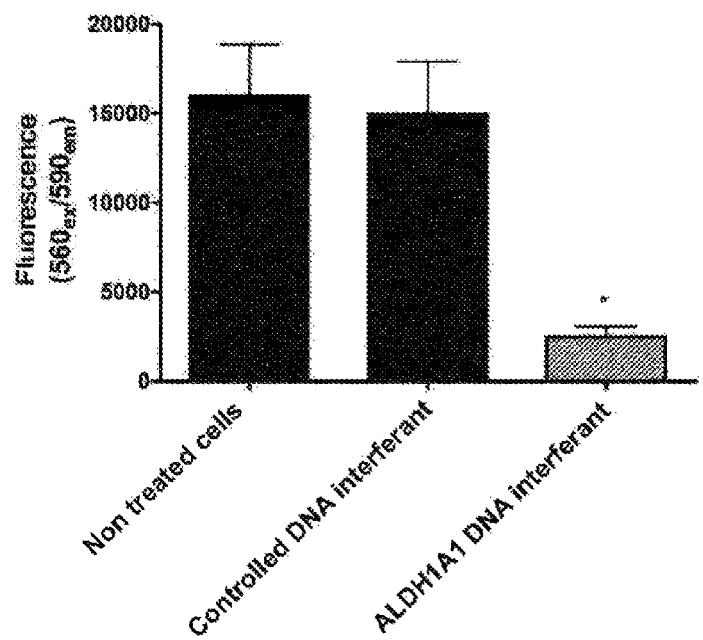
FIG. 2: Test of ALDH1 activity by resorufine propionate after treatment with ALDH1A1 interfering the RNA.
Figure 2:
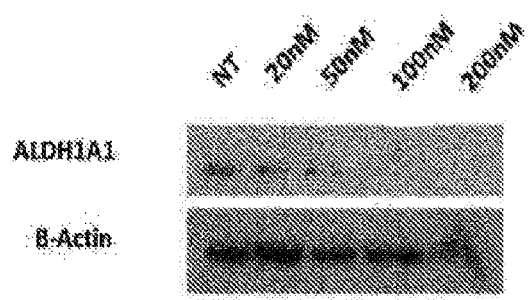

The results of the assay of ALDH1 activity by resorufine propionate after treatment with RNA interfering ALDH1A1 are illustrated in FIG. 2 which shows that a complete inhibition of ALDH1A1 is observed at 100 nM of siRNA which induces a decrease significant (P<0.05) signal resorufine propionate.

Figure 3:
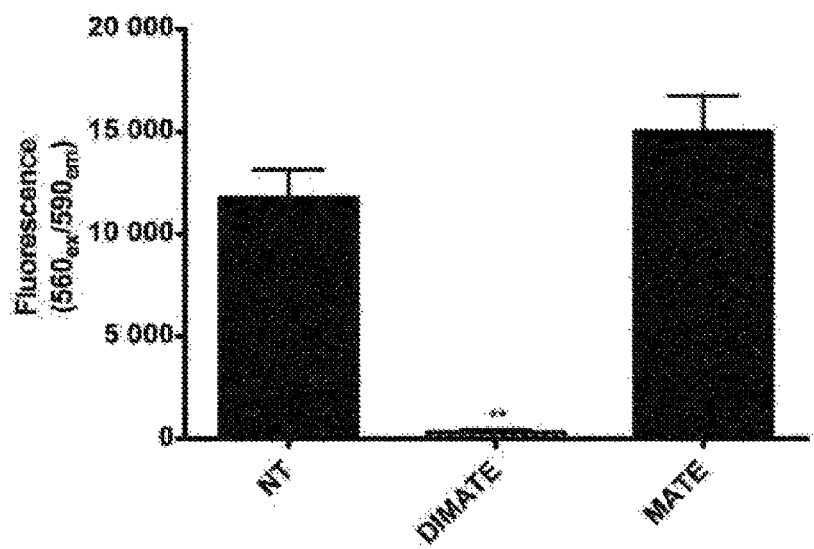
FIG. 3: Test of ALDH1 activity by resorufin propionate after treatment with inhibitors of ALDH 1 and 3.

The results of the test of ALDH1 activity by resorufin propionate after treatment with inhibitors of ALDH 1 and 3 are illustrated in FIG. 3 and shows a significant inhibition of fluorescence (P<0.001) after treatment with DIMATE (inhibitor of ALDH 1 and 3) unlike MATE which is a specific inhibitor of ALDH3.

In addition, the conversion of resorufin propionate to resorufin, a molecule that fluoresces in the red, was detected by fluorescent microscopy. The reaction is inhibited by DIMATE, an inhibitor of ALDH 1, showing the specificity of the substrate (results not shown). In addition, the fluorescent signal of resorufine propionate can be colocalized with ALDH1A1 suggesting specific activity with the enzyme (results not shown).

Figure 4:
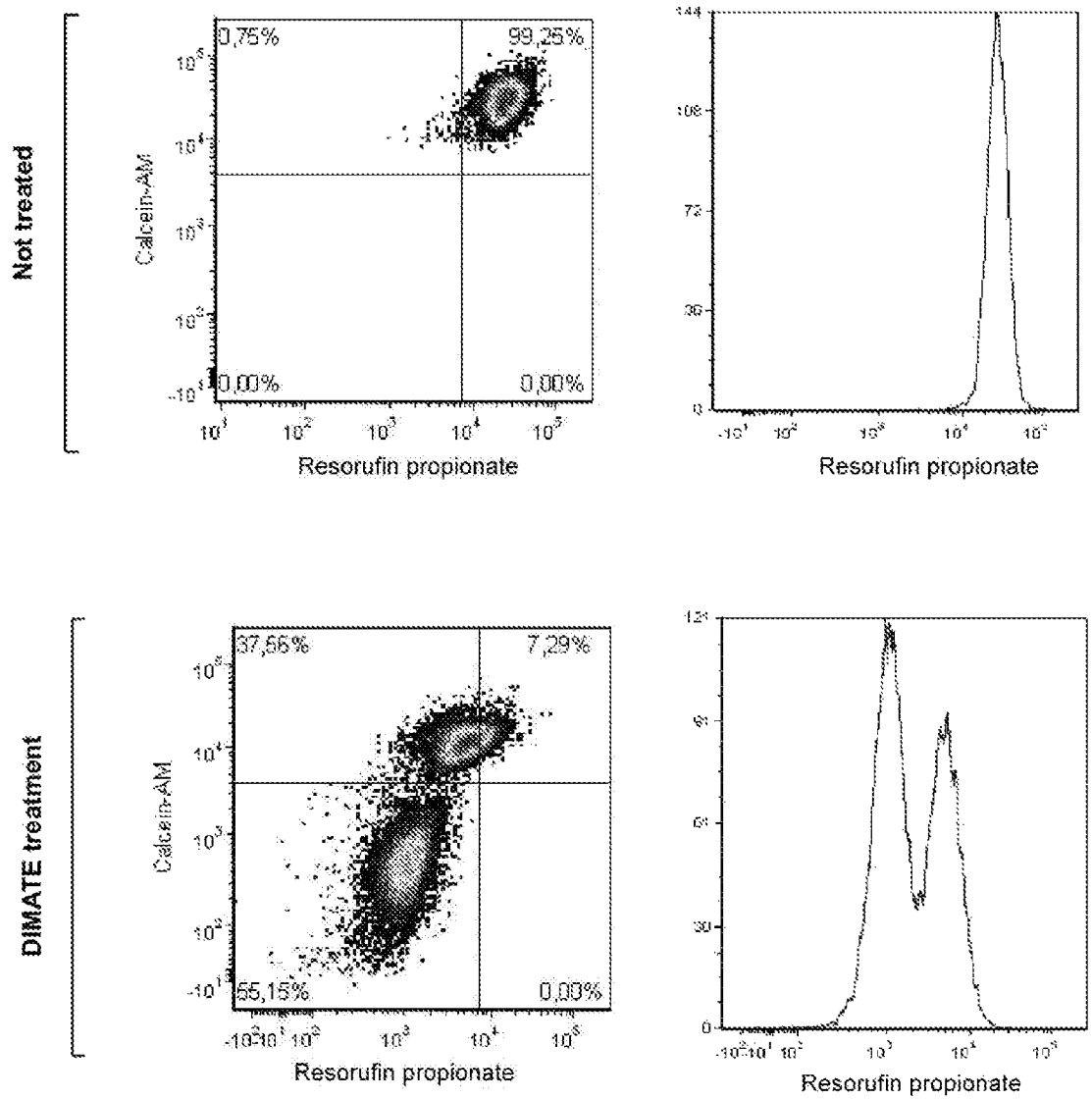
FIG. 4: ALDH1 activity detected by flow cytometry via resorufine propionate.

FIG. 4 illustrates ALDH1 activity detected by flow cytometry via resorufin propionate. The untreated condition demonstrates the presence of live positive ALDH1 cells (Calcein-AM).

In the presence of an inhibitor of ALDH1, DIMATE, positive ALDH1 cell inhibition is observed for living cells as well as a decrease in viability, due to treatment.

Figure 5:
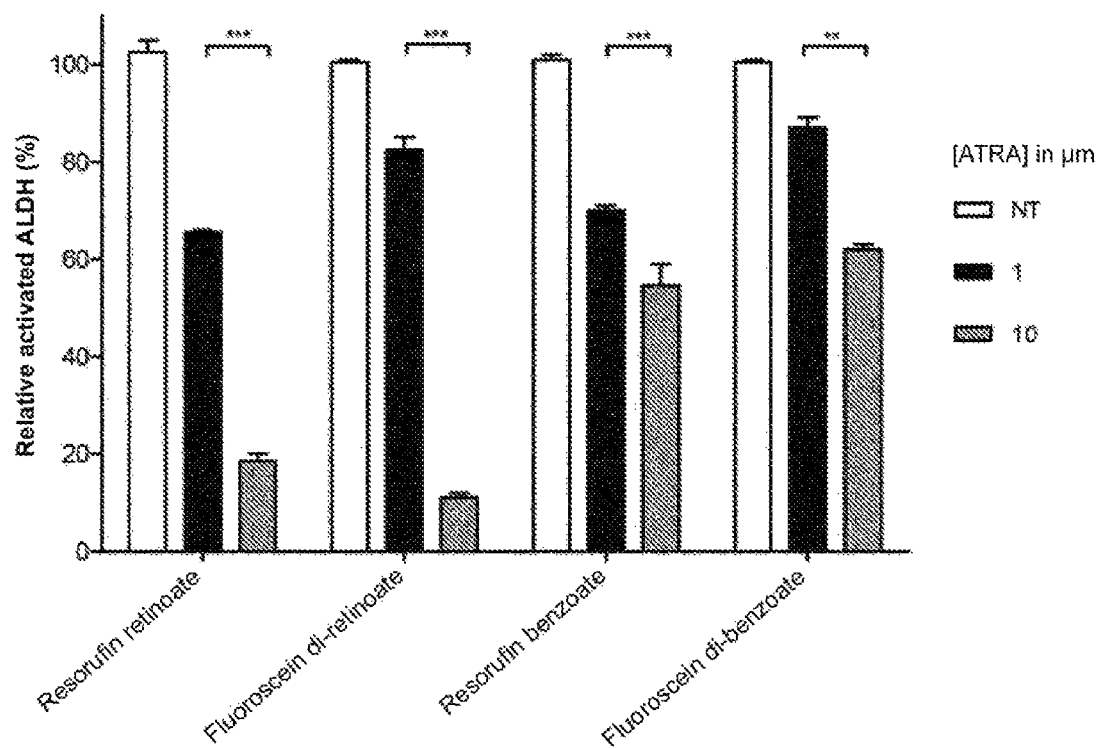
FIG. 5: Test of ALDH1 activity by resorufin retinoate and fluorescein di-retinoate and ALDH3 by resorufin benzoate and fluorescein dibenzoate after retinoic acid treatment.

Results of the test of ALDH1 activity by resorufin retinoate and fluorescein di-retinoate and ALDH3 activity by resorufin benzoate and fluorescein di-benzoate after retinoic acid treatment are illustrated by FIG. 5 which shows that a significant ($P<0.001$) or ($P<0.01$) level of activity inhibition of ALDH1 for resorufin retinoate and fluorescein di-retinoate and ALDH3 for benzoate of resorufin and fluorescein di-benzoate.

Figure 6:
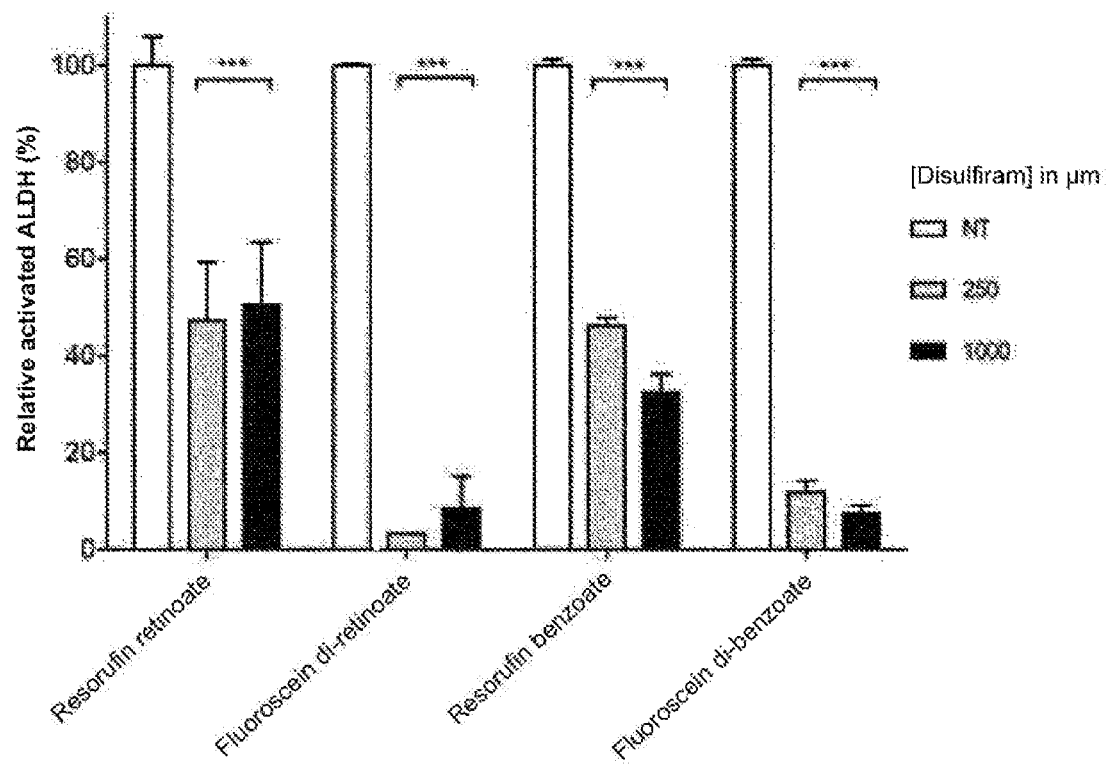
FIG. 6: Test of ALDH1 activity by resorufin retinoate and fluorescein di-retinoate, and ALDH3 by resorufin benzoate and fluorescein dibenzoate after Disulfiram (DSF) treatment.

In the presence of DSF at both the 250 nM and 1000 nM concentrations, a significant ($P<0.001$) inhibition of ALDH1 activity for resorufin retinoate and fluorescein di-retinoate and ALDH3 for resorufin benzoate and fluorescein di-benzoate, are illustrated in FIG. 6.

3. Application of the Use of Substrates

Materials and Methods

Patients

Bone marrow (Mo) and blood (Sg) were obtained from 33 patients with their enlightened chords. The evaluations were performed on whole blood after lysis of red blood cells or bone marrow.

Isolation of Blast Cells and Evaluation of ALDH1 and ALDH3 Activity

The isolation of the blast cells was performed by a Navios flow cytometer (Beckman Coulter®) according to the phenotype of the latter indicated in Table 5 (CD34+, CD117+ or CD45 weak).

The ALDH1 and ALDH3 activity was evaluated by incubating the reagents: resorufin retinoate or resorufin octanoate at 5 $\mu mol^{-1}$ and fluorescein di-retinoate or fluorescein dioctanoate at 0.8 $\mu mol^{-1}$ in the blood total after lysis of red blood cells or in bone marrow extract for 30 minutes at 37° C. The fluorescence observed is analyzed by cytometry making it possible to give a value of the median fluorescence intensity (MFI) corresponding to the relative activity of each ALDH isoform of the blast cells.

Results

The results are shown in Table 4 below.

TABLE 4

Patient parameters included in the study of the different activities of Aldehydes Dehydrogenases.

| Pt No | Age | Pathology | Type of sampling | Relapse (Y/N) | Phenotypes of blasts | Resorufin Retinoate (IFM) | Resorufin Octanoate (IFM) | Fluorescein di-retinoate (IFM) | Fluorescein octanoate (IFM) |
|---|---|---|---|---|---|---|---|---|---|
| 1 | 74 | LAM | Sg | Y | CD34 pos. | 59.47 | 11.05 | 147.18 | 65.23 |
| 2 | 50 | LAM | Sg | N | CD34 pos. | 34.98 | 10.26 | 56.44 | 34.07 |
| 3 | 50 | LAM | Mo | N | CD34 pos. | 129.14 | 20.1 | 104.36 | 214.5 |
| 4 | 44 | LAM | Sg | Y | CD34 pos. | 121.23 | 12.72 | 230.7 | 103.44 |
| 5 | 91 | LAM | Mo | Y | CD45 weak | 2.01 | 3.7 | 16.23 | 6.11 |
| 6 | 91 | LAM | Sg | Y | CD117 pos. | 69 | 61.13 | 299.48 | 37.47 |
| 7 | 82 | LAM | Sg | N | CD45 weak | 3.03 | 10.66 | | |
| 8 | 84 | LAM | Sg | N | CD45 weak | 2.08 | 25 | 151 | 9.05 |
| 9 | 93 | LAM | Sg | N | CD45 weak | 8.99 | 25.83 | 169 | 8.74 |
| 10 | 78 | LAM | Sg | N | CD45 weak | 1.5 | 1.93 | 27.5 | 3.55 |
| 11 | 67 | AREB | Mo | N | CD34 pos. | 40.46 | 20.32 | 72.4 | 9.5 |
| 12 | 74 | LAM | Sg | Y | CD34 pos. | 548 | 12.45 | 349 | 64 |
| 13 | 74 | LAM | Sg | Y | CD34 pos. | 83.29 | 6.5 | 91.03 | 245.88 |
| 14 | 80 | AREB | Sg | Y | CD34 pos. | 14.8 | 13.71 | 114.2 | 1.07 |
| 15 | 80 | AREB | Sg | Y | CD34 pos. | 86.29 | 5.94 | 144.98 | 87.99 |
| 16 | 71 | LAM | Sg | Y | CD34 pos. | 15.18 | 670 | 773 | 14.3 |
| 17 | 71 | LAM | Sg | Y | CD34 pos. | 74.79 | 8.82 | 139.26 | 94.44 |
| 18 | 39 | LAM | Mo | N | CD117 pos. | 160.58 | 11.53 | 119.1 | 176.9 |
| 19 | 39 | LAM | Mo | N | CD117 pos. | 59.03 | 8.01 | 54.01 | 25.93 |
| 20 | 39 | LAM | Sg | N | CD117 pos. | 252.73 | 4.35 | 28.27 | 422.55 |
| 21 | 53 | LAM | Sg | N/D | CD117 pos. | 66 | 78.82 | 246 | 35.26 |
| 22 | 53 | LAM | Mo | N/D | CD34 pos. | 64.7 | 8.02 | 33.11 | 2.87 |
| 23 | 53 | LAM | Mo | N | CD34 pos. | 26.71 | 568 | 2.41 | 17.67 |
| 24 | 53 | LAM | Mo | N | CD34 pos. | 83.04 | 14.64 | 131.04 | 78.47 |
| 25 | 78 | LAM | Sg | Y | CD34 pos. | 71.71 | 46.24 | 176.61 | 64.29 |
| 26 | 71 | LAM | Mo | Y | CD34 pos. | 101.54 | 11.6 | 144.5 | 64.3 |
| 27 | 93 | LAM | Sg | Y | CD34 pos. | 73.52 | 6.57 | 217.5 | 123.02 |
| 28 | 70 | AREB | Sg | Y | CD34 pos. | 97.79 | 9.79 | 112 | 48.19 |
| 29 | 60 | LAM | Mo | N | CD34 pos. | 171.6 | 13.23 | 74.26 | 133.5 |
| 30 | 70 | LAM | Mo | Y | CD34 pos. | 39.26 | 91.95 | 139.19 | 29.68 |
| 31 | 70 | LAM | Sg | Y | CD34 pos. | 34.26 | 15.22 | 101.1 | 26.3 |
| 32 | 72 | LAM | Sg | N | CD34 pos. | 25.06 | 4.08 | 27.7 | 19.04 |
| 33 | 72 | LAM | Mo | N | CD34 pos. | 70 | 3.58 | 25.66 | 33.82 |

AML, Acute Leukemia Myeloide; AREB, Refractory Anemia with Excess Blasts; Sg, blood; Mo, bone marrow; IFM, value of the Median Fluorescence Intensity.

The invention claimed is:

1. A method for quantifying at least one aldehyde dehydrogenase (ALDH) isoenzyme expressed by a cell population, comprising:
   (i) bringing the ALDH isoenzyme expressed by a cell population into contact with at least one specific substrate of an ALDH isoenzyme comprising a compound:
      (a) of formula (I): R—COO-A (I) resulting from the esterification of a fluorescent tracer A-OH with an acylating agent derived from the corresponding acid RCOOH, in which R is chosen in order to form a compound selected from the group consisting of retinoate, propionate, octanoate, benzoate, 4-aminobutyrate, hexanoate, 4-diethylaminobenzoate and 4-hydroxy-2-nonenoate; or
      (b) of formula (II):

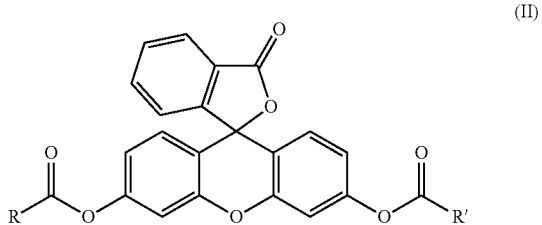

in which:
   R and R', which are identical or different, are chosen in order to form a compound selected from the group consisting of retinoate, propionate, octanoate, benzoate, 4-aminobutyrate, hexanoate, 4-diethylaminobenzoate and 4-hydroxy-2-nonenoate; and
   (ii) measuring the fluorescence of the fluorescent tracer released by the reaction between the ALDH isoenzyme and the at least one specific substrate.

2. A method for distinguishing healthy stem cells from cancer stem cells, the method comprising:
   (i) bringing an ALDH isoenzyme expressed by a cell population into contact with at least one specific substrate of an ALDH isoenzyme comprising a compound:
      (a) of formula (I): R—COO-A (I) resulting from the esterification of a fluorescent tracer A-OH with an acylating agent derived from the corresponding acid RCOOH, in which R is chosen in order to form a compound selected from the group consisting of retinoate, propionate, octanoate, benzoate, 4-aminobutyrate, hexanoate, 4-diethylaminobenzoate and 4-hydroxy-2-nonenoate; or
      (b) of formula (II):

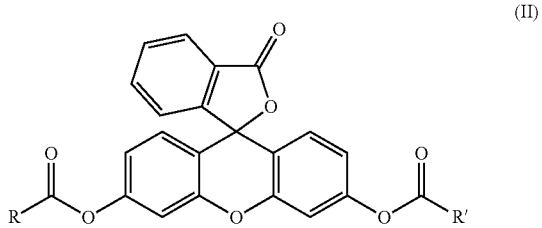

in which:
   R and R', which are identical or different, are chosen in order to form a compound selected from the group consisting of retinoate, propionate, octanoate, benzoate, 4-aminobutyrate, hexanoate, 4-diethylaminobenzoate and 4-hydroxy-2-nonenoate;
   (ii) measuring the fluorescence of the fluorescent tracer released by the reaction between the ALDH isoenzyme and the at least one specific substrate; and
   (iii) analyzing the fluorescence of the fluorescent tracer to determine the relative activity of the ALDH isoenzyme expressed by the cell population.

3. The method according to claim 2, wherein the method distinguishes healthy stem cells from stem cells from solid cancers and/or hematological malignant tumors.

4. A method for distinguishing cells expressing at least one ALDH isoenzyme in a cell population, wherein the method comprises:
   (i) measuring the fluorescence of a cell population that expresses an ALDH isoenzyme to obtain a first fluorescence;
   (ii) bringing the cell population that expresses an ALDH isoenzyme into contact with at least one specific substrate of an ALDH isoenzyme comprising a compound:
      (a) of formula (I): R—COO-A (I) resulting from the esterification of a fluorescent tracer A-OH with an acylating agent derived from the corresponding acid RCOOH, in which R is chosen in order to form a compound selected from the group consisting of retinoate, propionate, octanoate, benzoate, 4-aminobutyrate, hexanoate, 4-diethylaminobenzoate and 4-hydroxy-2-nonenoate; or
      (b) of formula (II):

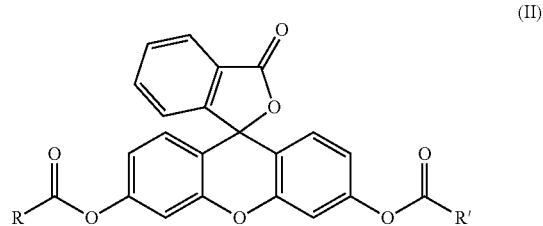

in which:
   R and R', which are identical or different, are chosen in order to form a compound selected from the group consisting of retinoate, propionate, octanoate, benzoate, 4-aminobutyrate, hexanoate, 4-diethylaminobenzoate and 4-hydroxy-2-nonenoate;
   (iii) measuring the fluorescence of the cell population that expresses an ALDH isoenzyme that has been brought into contact with the at least one specific substrate to obtain a second fluorescence; and
   (iv) comparing the first fluorescence and the second fluorescence to identify cells with increased fluorescence relative to the fluorescence of the cell population that expresses an ALDH isoenzyme before the cell population that expresses an ALDH isoenzyme is brought into contact with the at least one specific substrate of an ALDH isoenzyme.

5. The method according to claim 1, wherein A-OH is chosen from the group consisting of 7-hydroxycoumarin, a fluorophore of the tokyo green family, resorufin and fluorescein.

6. The method according to claim 1, wherein the ALDH isoenzyme is ALDH1 and wherein R and R', which are identical or different, are chosen in order to form a compound selected from the group consisting of retinoate, hexanoate and propionate.

7. The method according to claim 1, wherein the ALDH isoenzyme is ALDH3 and wherein R and R', which are identical or different, are chosen in order to form a compound selected from the group consisting of octanoate, the 4-hydroxy-2-nonenoate, the 4-diethylaminobenzoate and benzoate.

* * * * *